United States Patent
Kou et al.

(12)

(10) Patent No.: US 7,323,547 B2
(45) Date of Patent: Jan. 29, 2008

(54) HIGHLY EXPRESSED PEPTIDE OF WHITE SPOT SYNDROME VIRUS IN HOSTS AND APPLICATION THEREOF

(75) Inventors: Guang-Hsing Kou, Taipei (TW); Chu-Fang Lo, Taipei (TW); Han-Ching Wang, Taipei (TW); Wei-Pang Huang, Taipei (TW)

(73) Assignee: National Taiwan University, Da-an District, Taipei (TW)

( * ) Notice: Subject to any disclaimer, the term of this patent is extended or adjusted under 35 U.S.C. 154(b) by 0 days.

(21) Appl. No.: 11/438,235

(22) Filed: May 22, 2006

(65) Prior Publication Data

US 2007/0269453 A1 Nov. 22, 2007

(51) Int. Cl.
*C07K 14/00* (2006.01)
*C07H 21/04* (2006.01)

(52) U.S. Cl. .................... 530/350; 536/23.1

(58) Field of Classification Search ............... None
See application file for complete search history.

*Primary Examiner*—Bruce R. Campell
*Assistant Examiner*—Nicole E Kinsey
(74) *Attorney, Agent, or Firm*—Morris Manning Martin LLP; Tim Tingkang Xia, Esq.

(57) ABSTRACT

The present invention relates to a WSSV peptide, which comprises a peptide sequence as set forth in SEQ ID NO: 1 and can be used as target peptide for WSD immunodetection in crustaceans. In addition, the present invention also provides a WSSV nucleotide sequence, which comprises a nucleotide sequence encoding the peptide sequence as set forth in SEQ ID NO: 1, and can be used as a detection target for WSD in crustaceans. On the other hand, the present invention can be applied in a WSSV detection method using the peptide or nucleotide sequences as targets. The WSSV peptide of the present invention is highly expressed in the hosts. The sensitivities of the WSSV detection using the target peptide in the invention are therefore greatly increased in comparison to the traditional detection target.

13 Claims, 5 Drawing Sheets

HIGHLY EXPRESSED PEPTIDE OF WHITE SPOT SYNDROME VIRUS IN HOSTS AND APPLICATION THEREOF

BACKGROUND OF THE INVENTION

1. Field of the Invention

The present invention relates to a peptide of virus for crustaceans, especially relates to a peptide of white spot syndrome virus (WSSV), which highly expressed in their hosts.

2. The Prior Arts

Aquaculture is an important industry in most of the Asian countries. However, it has been threatened by several virus-induced diseases recently because of high-density cultivation. White spot disease (WSD) is one of the major diseases causing tremendous economic losses in aquaculture industry. The most observed clinical sign of WSD is white spots in the exoskeleton in diseased shrimp, especially in the head region (cephalothorax). White spot syndrome virus (WSSV) is the causative pathogen of WSD, which can cause high infectivity and high mortality of infected shrimps. WSSV has a wide host range among crustaceans, included many species of cultured and wild shrimp, crab, crayfish, lobster. Crabs are reservoir hosts for the WSSV virus because of their tolerance. The cumulative mortality rate can reach 100% for the WSSV-infected shrimps within 2 to 10 days from the onset of gross visible signs. The high morbidity and high mortality qualities of WSD were received high attention for scientists and fisheries. WSD was first reported in a commercial shrimp production facility in Fu-Jian province of Mainland China in 1992, and subsequently found in many Asian countries including Taiwan, Korea, Thailand, Japan, India, the Philippines and Indonesia. For more than 10 years, WSD has been identified from Asia to the whole world, such as America. The damage has been made to all the shrimp production areas. Therefore, WSD is not only health threat to the crustaceans, but also results in devastating economic losses for aquaculture farmers.

To prevent and control WSD disease, global hatchery managers have to monitor the progress of the disease and detect the infection of WSSV in the aquaculture crustaceans during cultivation regularly. Nested Polymerase Chain Reaction (nested PCR) is a sensitive and specific diagnostic too and now commercially available for many viruses of aquaculture crustaceans, including WSSV.

Nested PCR uses two sets of amplification primers. The first pair of primer amplified a larger PCR product. Then a second PCR reaction is run with the second pair of primers using the product of the first reaction as the amplification target. This procedure increases the sensitivity of the assay, which is suitable for detection of low template concentration. Therefore it can be applied in analysis of trace quantities of DNA. However, nested PCR diagnostic kits are routinely used in research laboratories, the associated costs and the technical expertise required have prevented their widespread adoption in traditional aquaculture farmers.

Therefore, it would be helpful to develop a diagnostic test that was not only highly sensitive and rapid, but also cheap and easily performed. An immuno-based detection system is suggested for such a test. This test used a specific protein of virus as the detection target. Higher expression levels of target protein lead this immunodetection test more sensitive, even when viral titers are low in the hosts. Hence, target protein is the key element for the immunodetection technique. The expression of WSSV envelope protein VP28 is known to be the target protein for immunodetection. VP28 is regarded as the most highly expressed protein in WSSV in the past, but the expression level of VP28 is far beyond that of host proteins. Practically the application of VP28 in WSSV detection for crustaceans is limited by the amount unless being seriously infected.

SUMMARY OF THE INVENTION

A primary object of the present invention is to provide a WSSV peptide highly expressed in hosts, which comprises a peptide sequence as set forth in SEQ ID NO: 1 and can be used as target peptide for WSD immunodetection.

Another object of the present invention is to provide a WSSV nucleic acid fragment, which has a nucleotide sequence encoding the peptide sequence as set forth in SEQ ID NO: 1, and the nucleotide sequence is set forth in SEQ ID NO: 2.

The abovementioned WSSV peptide can be obtained by constructing a recombinant plasmid comprising a nucleotide sequence encoding the above peptide sequence and transforming this recombinant plasmid into a host cell (expression host bacteria strains). The plasmid for expressing preferably is the pET Expression System; more preferably is pET28b plasmid. The host strain preferably is *Escherichia coli*; more preferably is *Escherichia coli* strain BL21 (DE3) codon plus.

Yet another object of the present invention is to provide a method for detecting the WSSV, which comprises the following steps:

(a) preparing a reagent, which comprises antibodies against the peptide as set forth in SEQ ID NO: 1;
(b) providing a tissue sample from an organism;
(c) contacting the tissue sample to the reagent, and producing complexes of the antibodies and peptide as set forth in SEQ ID NO: 1 in the tissue sample of the organism; and
(d) detecting the complexes to determine whether the organism was infected by the WSSV.

Still another object of the present invention is to provide a method for detecting the WSSV, which comprises the following steps:

(i) providing a DNA microarray chip, which comprises a probe that can bind a nucleic acid fragment, and the nucleic acid fragment comprises a nucleotide sequence as set forth in SEQ ID NO: 2 that encode the peptide of the WSSV;
(ii) providing a tissue sample from an organism;
(iii) performing a hybridization reaction of a nucleic acid extracted from the tissue sample and the probe; and
(iv) detecting the nucleic acid fragment in the tissue sample to determine whether the organism was infected by the WSSV.

Another method for detecting the WSSV in the present invention comprises the following steps:

(I) providing a RT-PCR (reverse transcription-PCR) detection system, which comprises a mixed reagent containing primer for cDNA synthesis and primer pairs that can amplify a nucleic acid fragment which comprises a nucleotide sequence as set forth in SEQ ID NO: 2 that encode the peptide of the WSSV;
(II) providing a tissue sample from an organism, extracting its RNA, and reverse transcribing the RNA into complementary deoxyribonucleic acid (cDNA);
(III) performing a PCR reaction using the cDNA of the tissues sample and the mixed reagent to amplify the nucleotide sequence; and (IV) detecting the nucleotide sequence in the tissue sample to determine whether the organism was infected by the WSSV.

The organism describing above is the host that can be infected by the WSSV or is susceptible to the WSSV. The examples of the host include but not limited to aquaculture crustaceans. The examples of the aquaculture crustaceans include but not limited to shrimp and crabs.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Example 1

Figure 1:
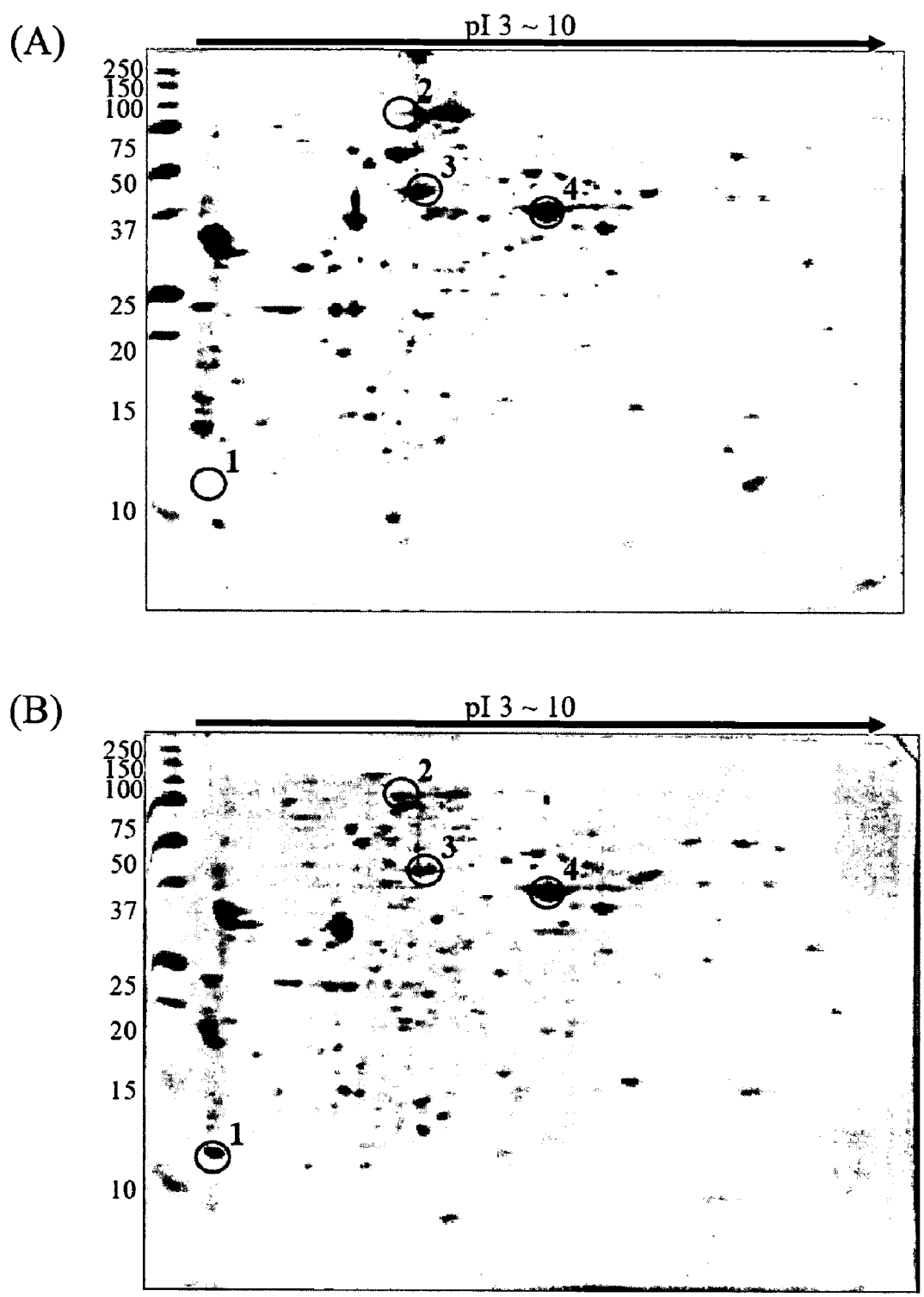
FIG. 1. Two-dimensional gel electrophoresis profiles of the cytoplasmic proteins in L. vannamei stomachs. (A) 2-D profiles of the control group (PBS injection); (B) 2-D profiles of the WSSV-infected group. Spot 1: virus WSSV ICP11 protein; pI: isoelectric point.

DNA Microarray Screening for Highly Expressed WSSV Genes in the Hosts

WSSV DNA microarray chips were prepared as described by Wang et al (Wang et al., 2004, Marine Biotechnology 6, S106-S111), Tsai et al. (Tsai et al., 2004, Journal of Virology 78, 11360-11370) or Liu et al. (Tsai et al., 2005, Virology 78, 11360-11370). There are 532 WSSV open reading frame (ORFs) and one shrimp (Penaeus monodon) β-actin gene in the chip. Total RNA was extracted from gill tissues of WSSV-infected shrimps at 0 and 24 hpi (hour post infection). RNA samples (20 μg for each reaction) were reverse-transcribed and fluorescently labeled with Cy3dUTP using a CyScribe First-Strand cDNA-labeled kit (Amersham). After the Cy3-labeled complementary deoxyribonucleic acid (cDNA) targets were concentrated, the unincorporated nucleotides were removed using Microcon YM-30 columns (Amicon). The samples were subjected to hybridization with all of the DNA spots in the WSSV DNA microarray chip. The microarrays were scanned with a confocal laser ScanArray 3000 system and the fluorescence intensities in each spot were quantified using Imagen 4.0 (Biodiscovery, Inc.). The signal intensities were normalized to control the background and have normalized signal intensity using the expression of β-actin gene as the normalization factor. The expression of each gene (transcript) in the WSSV-infected gill tissues of shrimps was shown as a percentage based on the expression of β-actin gene. From the results of DNA microarray, icp11 (SEQ ID NO: 2) was shown to be the highly expressed gene in the WSSV-infected gill tissues of shrimps.

Example 2

Expression Sequence Tag (EST) Screening for Highly Expressed WSSV Genes in the Hosts A single cDNA library, PmTwI, which was constructed using WSSV-infected P. monodon postlarvae (PL20) and a λ-Zap II vector construction kit (Stratagene) according to the manufacturer's instructions, were converted to pBluescript-based plasmid libraries following the mass excision protocol provided by Stratagene. A total of 7632 ESTs were obtained from the library after randomly subcloning of the clones and 3'-end sequence analysis. Quality control of sequenced ESTs was performed using assembly of the program Phred and the program cross-match with default parameters (minimatch 12, penalty −2, minscore 20) to yield a total of 2237 unique sequences in PmTwI. These sequences were examined for matches in the GeneBank nr (non-redundant) peptide sequence database and SWISS PROT using BlastX and InterPro Scan with default parameters. From the 2237 unique sequences, 48 WSSV genes were identified. Among them, icp11 was the most strongly expressed gene (EST redundancy=29), which is 4 times of the expression levels of VP28. Both the screening results from DNA microarray chips and expression sequence tags showed that icp11 expressed to a large scale in the hosts (Table 1).

Example 3

Two-Dimensional Gel Electrophoresis and Protein Identification for Highly Expressed WSSV Genes in the Hosts Stomachs from WSSV-infected shrimp (Litopenaeus vannamei; mean body weight: 2.6 g) were frozen in liquid nitrogen, homogenized and suspended in a Lysis-PBS buffer (PBS diluted 3× in ddH$_2$O at 4° C.) containing protease inhibitor cocktail (Roche Diagnostics, Mannheim, Germany). After centrifugation (3,000 g; 30 min, 4° C.), the supernatant (i.e. the cytosolic protein fraction) was collected. Trichloroacetic acid (TCA; 20% w/v) was added to the supernatant to a final concentration of 10% w/v and the solution was allowed to stand on ice for 30 min. The supernatant was discarded and the pellet resuspended in acetone containing 0.1% dithiothreitol (DTT) after centrifugation (10,000 g, 30 min, 4° C.). The resulted solution was centrifuged again (10,000 g, 30 min, 4° C.), to obtain pellet, which was dried under vacuum and then rehydrated with rehydration buffer (9.8 M urea, 2% 3-[(3-cholamidopropyl) dimethylammonio]-1-propanesulfonic acid (CHAPS), 20 mM DTT, 0.5% IPG buffer [pH 4-7 or 3-10; Amersham Biosciences]). After a final centrifugation (10,000 g, 30 min, 15° C.), the supernatant containing the soluble protein fraction was loaded into a 2-D electrophoresis (2-DE). Protein concentration of the samples was determined using a 2-D Quant Kit (Amersham Biosciences). The first dimension of the 2-DE, isoelectric focusing (IEF), was performed in a 13 cm Immobiline DryStrip gel (Amersham Biosciences) using an integrated system, the Ettan IPGphor (Amersham Biosciences), where rehydration of the samples and IEF were performed automatically. Each sample (250 µg protein) was dissolved in 250 µl rehydration buffers and placed in the base well of an IPGphor stripholder. An IPG strip was then placed on the top of the sample, and after rehydration in the IPGphor (16 h at 50 V), automatic IEF was performed using the following step voltage focusing protocol: 1 h at 300 V, 1 h at 500 V, 2 h at 1000 V, 2 h at 4000 V and 10 h at 8000 V. After the first dimensional IEF, the IPG strips were equilibrated in a sodium dodecyl sulfate (SDS) equilibration buffer (6M urea, 2% SDS, 30% glycerol, 50 mM Tris-HCl, pH 8.8) containing 1% DTT for 15 min. The IPG gel strips were then removed to another equilibration buffer containing 2.5% iodoacetamide and equilibrated for a further 15 min. Next, the equilibrated IPG strips were placed onto a polyacrylamide gel that consisted of a 14% acylamide separating gel (pH 8.8), and a 4% acylamide stacking gel (pH 6.8). The second dimensional separation was carried out at 20 mA per gel at 15° C. for 5-6 hours. The gels were stained with sypro ruby after electrophoresis, and the protein patterns of the gels were scanned using a Typhoon 9400 scanner (Amersham Biosciences). Gel image matching was performed using PDQuest software (Bio-Rad). Protein spots of interest were excised from the gels, washed twice with 25 mM ammonium bicarbonate buffer (pH 8.5) in 50% acetonitrile, for 15 min each time, dehydrated with 100% acetonitrile for 5 min, dried under vacuum, and digested with 100 ng of sequencing-grade, modified trypsin (Promega) in 25 mM ammonium bicarbonate (pH 8.5), at 37° C. for 16 h. Following digestion, tryptic peptides were extracted twice with 5% formic acid in 50% acetonitrile for 15 min each time and pooled for concentration to dryness under vacuum. Extracted peptides were dissolved in 50% acetonitrile containing 0.1% formic acid and analyzed with LC-nanoESI-MS/MS. The results were compared with the peptide sequence databases such as *Penaeus monodon* EST database, SWISS-PROT and NCBI.

The result of 2-DE is shown in FIG. 1, wherein (A) is from the control group and (B) is from the WSSV-infected samples. Spot 1 shown in FIG. 1 is ICP11 peptide (11 kDa) of WSSV, which is in markedly higher levels of expression than any other WSSV virus protein (FIG. 1). Quantitative image analysis using PDQuest software (Bio-Rad) revealed that the accumulated WSSV ICP11 protein level increased by more than 100 folds. These 2-DE results for WSSV ICP11 were in good agreement with those from the EST database and DNA microarray results to suggest that ICP11 is highly expressed at both the transcriptional and translational levels.

Example 4

Sequence Analysis of the 5'- and 3'-Termini of the icp11 Gene

RNA samples were extracted from the tissues of shrimp 36 h after WSSV infection, and the 5' and 3' untranslated regions of the WSSV icp11 transcript were obtained by rapid amplification of the cDNA 5'/3' ends using a commercial 5'/3' Rapid Amplification of cDNA Ends kit (RACE kit) with an avian myeloblatosis virus (AMV) reverse transcriptase. The 5' RACE protocol was slightly modified for WSSV icp11 because the 5' untranslated region incorporates long stretches of thymidines, which may cause the non-specific binding of the oligo (dT)-anchor primer to the cDNA. Accordingly, the cDNA of WSSV icp11 was 3'-tailed with dCTPs rather than dATPs, and the oligo (dG)-anchor primer was used in the PCR reaction. The PCR products were cloned into pGEM-T Easy vector and the sequences were analyzed.

Figure 2:
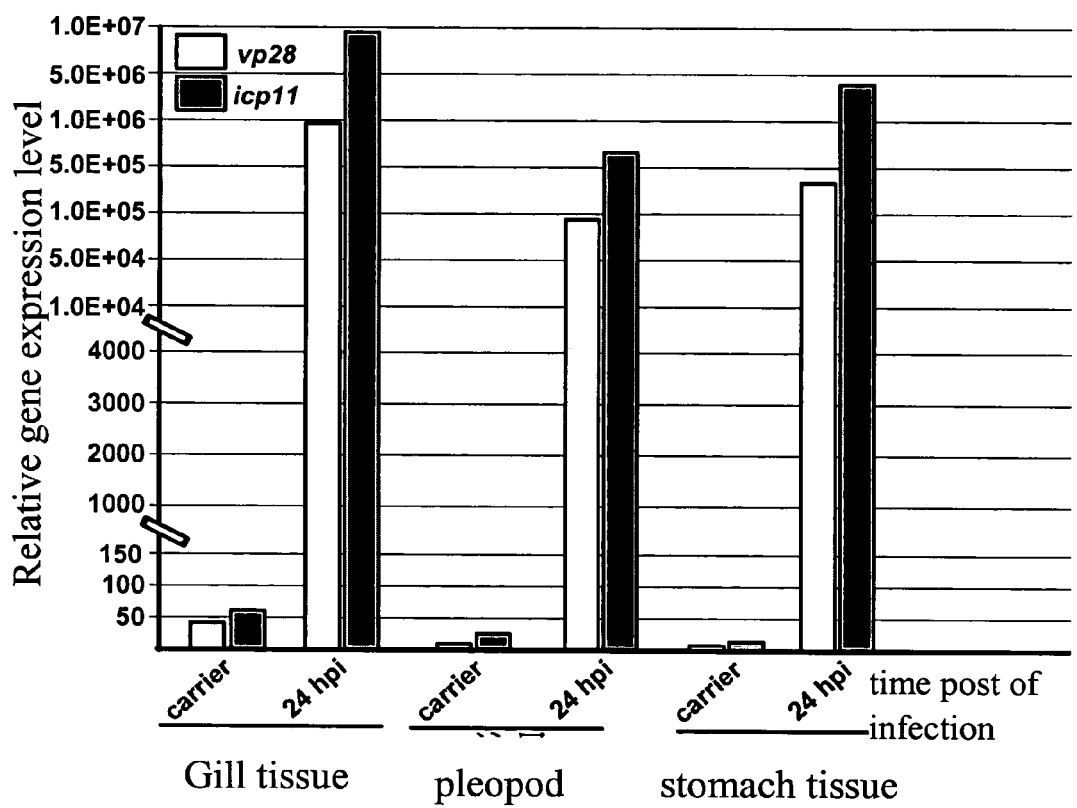
FIG. 2. The Real time RT-PCR analysis of WSSV-infected shrimps at different times post infection. RT-PCR primers were WSSV icp11, and vp28.

Sequencing result showed that open reading frame (ORF) of the icp11 comprises 249 nucleotides as set forth in SEQ ID NO: 2, with the potential to encode a 82 amino acid containing peptide sequence as set forth in SEQ ID NO: 1. Real time RT-PCR analysis at different time post infection revealed that the transcripts of WSSV icp11 is expressed to a large extent and is higher than the expression levels of WSSV envelope protein VP28 gene (FIG. 2). WSSV icp11 gene exhibits high expression levels, which may be monitored with other crustaceans' virus after reverse transcription to increase the sensitivity and efficiency for WSSV detection.

On the other hand, the known DNA microarray can be used to screen the SEQ ID NO: 2 containing DNA fragment in lots of samples from crustaceans to determine the infection of WSSV. For example, RNA samples of crustaceans extracted were reverse-transcribed and fluorescently labeled to be the sample targets. The sample targets were subjected to hybridization with all of the DNA spots in the WSSV DNA microarray chip. Then, the signal intensities of each point on the chip were normalized. The WSSV infection levels in these crustaceans were recorded.

Example 5

Preparation of the Recombinant ICP11 Protein

The amplified WSSV icp11 fragment was digested with restriction enzymes of NdeI and XhoI and ligated into the NdeI and XhoI digested sites of pET28b vector to generate a WSSV ICP11 expression plasmid. The WSSV ICP11 recombinant protein (rICP11) was hyper-produced in *Escherichia coli* strain BL21 (DE3) codon plus after plasmid transformation and induction with 0.1 mM isopropylthiogalactoside (IPTG) at 37° C. for 1 hour. Following centrifugation, *E. coli* cell pellets were resuspended in lysis buffer containing 50 mM of $NaH_2PO_4$, 300 mM of NaCl, and 10 mM of imidazole (pH8.0). The cells were sonicated on ice bath and the lysate was centrifuged to remove the cell debris. The supernatant was loaded onto a Ni-NTA agarose column and washed with washing buffer (50 mM $NaH_2PO_4$, 300 mM NaCl, 20 mM imidazole, pH8.0). The rICP11 was eluted with elution buffer (50 mM NaH2PO4, 300 mM NaCl, 500 mM imidazole, pH8.0). The rICP1'-containing fractions were collected, pooled and dialyzed against PBS buffer. This protein was used to produce antibodies and be a positive control factor of immuno-based detection system.

Antibody of WSSV ICP11 can be produced using traditional methods. For example, the abovementioned rICP11 protein is injected into rabbit to induce immune reaction, and the serum from immunized rabbit is collected to purify the anti-ICP11 antibodies. The antibodies can be applied in immuno-based detection system for detecting the WSSV infection in crustaceans.

Example 6

Detection of the ICP11 Peptide Using Western Blot Analysis and Protein Dot-Blot Analysis Tissue samples were taken from the lymphoid organ, stomach, midgut, heart, gill, epidermis, pleopod, hepatopancreas and nervous tissue of WSSV-infected shrimp (*P. monodon*) at 48 h after infection. The tissue samples were homogenized in Lysis-PBS buffer (PBS diluted 3× in ddH$_2$O at 4° C.) and centrifuged (13,000 g, 15 min) to collect the supernatant. Supernatant samples (24 μg total protein) were separated on a 17.5% SDS-PAGE and transferred onto a Polyvinylidene Fluoride (PVDF) membrane with a semidry blotting system. The PVDF membrane was incubated for 16 hours at 4° C. in blocking buffer (5% skimmed milk and 3% normal goat serum in TBST [0.5% Tween 20, 200 mM NaCl, 50 mM Tris-HCl, pH7.5]), followed by 1 hours of incubation at room temperature in blocking buffer containing the anti-rICP11 polyclonal antibody diluted 1:5000. Two room temperature washes with Tris buffered saline containing Tween 20 (TBST 20) buffer were performed after incubation with antibody, and the membrane was incubated for 1 hour in blocking buffer containing horseradish peroxidase (HRP)-conjugated secondary antibody diluted 5,000 at room temperature and then washed two times with TBST buffer at room temperature. Immunoreactive proteins were detected using an enhanced chemiluminescence system (NEN life products, Inc.).

The gill tissue samples from *P. monodon* were also subjected to protein dot-blot analysis. A PVDF membrane was soaked in methanol for 5 min and mounted into a dot blot hybridization instrument (Minifold I 96-well Dot-blot system, Schleicher-Schuell Inc.). The total protein lysates of the gill tissue samples from shrimps were serially diluted (from 200 μg to 0.05 μg) and vacuum blotted onto the abovementioned PVDF membrane. Antibody incubation and method for detection were the same as described above for Western blot analysis.

Figure 3:
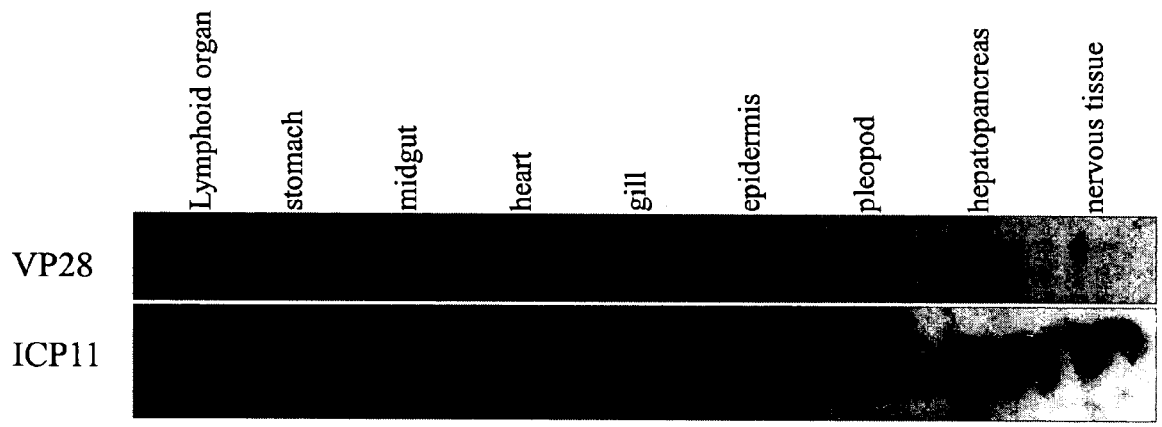
FIG. 3. Protein expression levels of ICP11 and VP28 after western blot analysis in different organs of WSSV-infected shrimp at 48 h post infection.

The results of Western blot analysis revealed that the ICP11 protein could be detected in all the tissues being tested, including pleopods and gills, where great amounts of ICP11 were shown (FIG. 3). Therefore, one gill filament or one pleopod is sufficient for virus detection, which is not life-threatening to the animals being tested.

Figure 5:
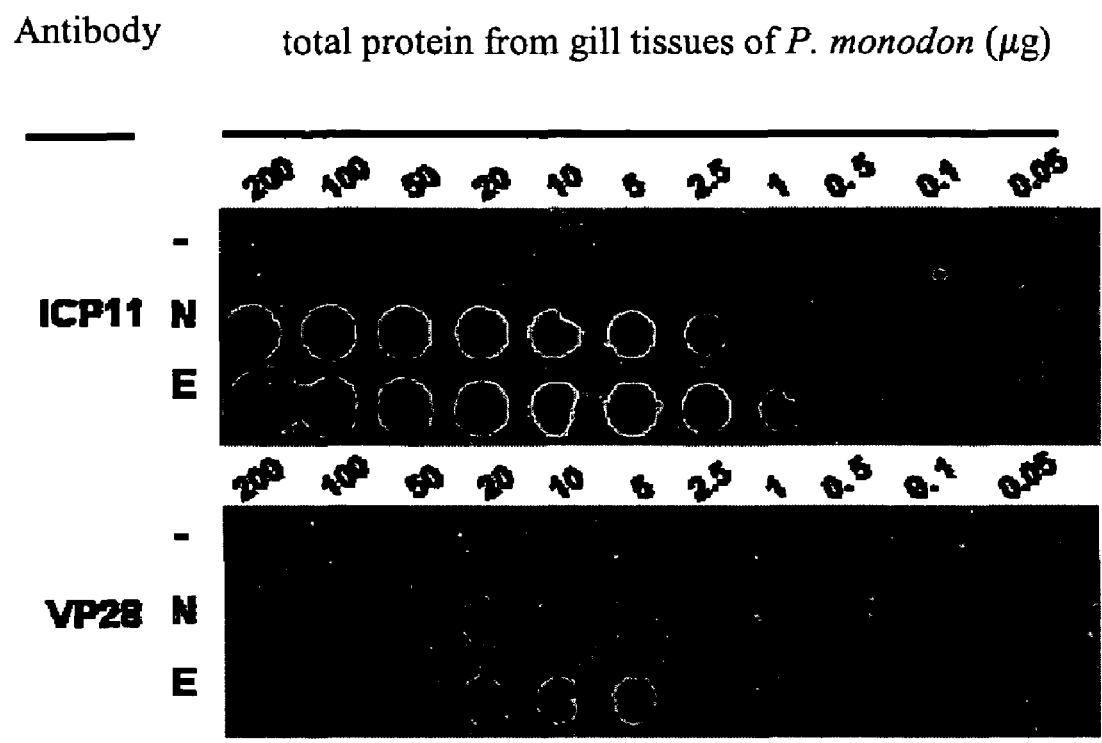
FIG. 5. Protein expression levels of ICP11 and VP28 after dot-blot analysis with antisera of ICP11 in shrimp gill tissues. "–": healthy P. monodon, "N": naturally WSSV-infected P. monodon, "E": WSSV-infected P. monodon experimental.

The results of dot-blot analysis showed that the minimal concentration of the specific anti-ICP11 antibodies, which could be detected, was starting from 1 μg in order to be clearly recognized (FIG. 5). Hence the detection of infection from WSSV is very sensitive. Using ICP11 as a detection target showed a higher sensitivity compared to that of VP28 for the detection of WSSV infection.

Example 7

Indirect Immunofluorescence Assay of WSSV ICP11

Figure 4:
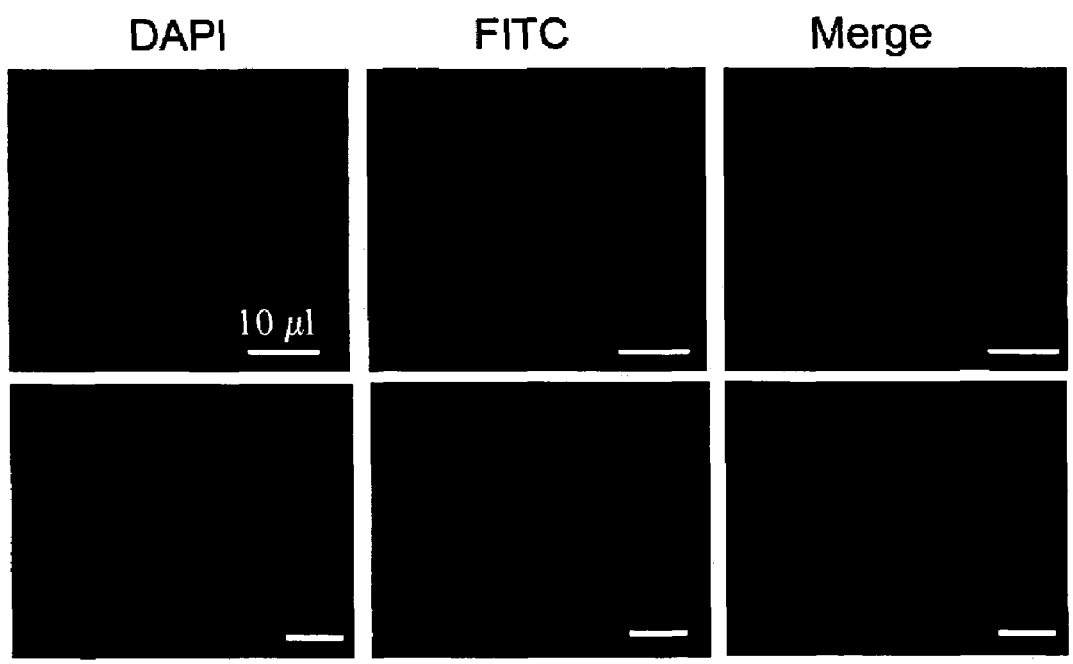
FIG. 4. Detection of WSSV ICP11 through indirect immunofluorescence assay.

Hemolymph was collected from healthy shrimps and from WSSV-infected shrimps at 24 h after infection using a syringe that contained cold modified Alsever's solution (MAS, Rodriguez et al., 1995). Hemolymph was placed on glass coverslips, washed with PBS buffer, and fixed in 4% paraformaldehyde for 10 min at 4° C. After 3 min acetone treatment on ice bath, the hemolymph was incubated with 3% normal goat serum for 16 hours at 4° C. to prevent non-specific antibody adsorption. The hemolymph was incubated for 3-4 hours at room temperature with a 1:500 dilution of rICP11-specific rabbit antiserum after blocking. Following two 15-min washes in PBS buffer containing 0.3% Tween-20 (PBST), the cells were incubated for 1 hour with a 1:200 dilution of fluorescein isothiocyanate (FITC-conjugated polyclonal goat anti-rabbit IgG Following washing with PBST, the cells were mounted and viewed under an Olympus microscope. The 4, 6-diamidino-2-phenylindole (DAPI) was used to counterstain the nucleus. Results showed that WSSV ICP11 was located in both the cytoplasm and the nucleus of hemocytes at 24 h post-infection (FIG. 4) Therefore, the indirect immunofluorescence assay can also be applied for the detection of WSSV infection in crustaceans.

Comparison Example 1

Detection of VP28 Using Western Blot Analysis and Dot-Blot Analysis

Detection of WSSV VP28 was carried out through Western blot analysis and dot-blot analysis as described in Example 6. The result of Western blot analysis showed that VP28 could not be detected in hepatopancreas and nervous tissue, and the expressions of VP28 in other tissues were much lower than those of ICP11 (FIG. 3).

The dot blot analysis showed that the VP28 detected, using the same samples from gills and the same exposure times, was far below that of ICP11. The minimal concentration of VP28, which could be detected, was from 5 μg to 200 μg of total soluble protein samples of shrimp gills. Therefore, both the results from Western blot analysis and dot-blot analysis showed that ICP11 is a better target than VP28, and can be sensitively detected for WSSV infection in crustaceans.

Through the above embodiments and examples, the present invention disclosed above provides an ICP11 peptide and its encoding nucleotide sequences to be used as target peptide or DNA sequences for detection of WSSV, which could be detected in the early phases of infection and are highly expressed in their hosts. The sensitivities of the WSSV detection are therefore greatly increased.

TABLE 1

Expression sequence tag (EST) screening for highly expressed WSSV genes in the hosts

| Open reading frame of WSSV[a] | EST repetitiveness[b] | Open reading frame of WSSV[a] | EST repetitiveness[b] |
|---|---|---|---|
| ICP11 | 29 | ICP56 | 2 |
| vp35 | 11 | ICP12 | 1 |
| vp19 | 10 | ICP96 | 1 |
| ICP23A | 8 | vp38A | 1 |
| vp28 | 8 | ICP137 | 1 |
| vp15 | 8 | ICP13A | 1 |
| ICP22 | 7 | ICP53 | 1 |
| ICP34 | 6 | ICP160 | 1 |
| ICP26 | 6 | ICP57 | 1 |
| ICP67 | 5 | ICP16 | 1 |
| ICP55 | | ICP90 | 1 |
| ICP31 | 5 | ICP13B | 1 |
| ICP50 | 4 | vp51B | 1 |
| VP75 | 4 | ICP174 | 1 |
| vp26 | 4 | ICP259 | 1 |
| ICP23B | 3 | ICP7 | 1 |
| ICP98 | 3 | ICP28 | 1 |
| ie1 | 3 | ICP32 | 1 |
| vp12B | 3 | ICP52 | 1 |
| ICP58 | 3 | ICP15 | 1 |
| ICP12 | 3 | ICP103 | 1 |
| ICP71 | 3 | ICP23C | 1 |
| ICP30 | 2 | ICP10 | 1 |
| ICP59 | 2 | ICP109 | 1 |
| ICP89 | 2 | | |

[a]Based on the WSSV isolated in Taiwan (GenBank accession no. AF440570).
[b]Each EST repetitiveness is determined from the database of WSSV-infected postlarvae shrimps.

What is claimed is:

1. An isolated peptide of white spot syndrome virus (WSSV), which is a highly expressed viral protein of the WSSV in hosts, comprising the peptide sequence as set forth in SEQ ID NO:1.

2. The peptide of WSSV as claimed in claim 1, wherein the hosts are susceptible to WSSV.

3. The peptide of WSSV as claimed in claim 2, wherein the hosts are shrimps.

4. The peptide of WSSV as claimed in claim 2, wherein the hosts are crabs.

5. The peptide of WSSV as claimed in claim 1, wherein the peptide can be prepared by a method comprising the steps of:
   (1) providing a nucleotide sequence encoding the peptide sequence as set forth in SEQ ID NO:1;
   (2) providing an expression vector which can express the peptide sequence as set forth in SEQ ID NO:1;
   (3) providing a host cell which can be used to express the peptide sequence as set forth in SEQ ID NO:1;
   (4) constructing the nucleotide sequence together with the vector to form a recombinant plasmid;
   (5) expressing the recombinant plasmid in the host cell to produce the peptide sequence as set forth in SEQ ID NO:1; and
   (6) recovering the peptide sequence as set forth in SEQ ID NO:1.

6. The peptide of WSSV as claimed in claim 5, wherein the vector is a vector of the pET expression system.

7. The peptide of WSSV as claimed in claim 5, wherein the vector is the pET28b expression vector.

8. The peptide of WSSV as claimed in claim 5, wherein the host cell is *Escherichia coli*.

9. The peptide of WSSV as claimed in claim 5, wherein the host cell is *Escherichia coli* strain BL21 (DE3) codon plus.

10. An isolated nucleic acid fragment of WSSV, which has the nucleotide sequence encoding the peptide sequence as claimed in claim 1.

11. The nucleic acid fragment as claimed in claim 10, wherein the nucleotide sequence is set forth as SEQ ID NO:2.

12. A method for detecting the WSSV, which comprises the following steps:
   (i) providing a DNA microarray chip, which comprises a probe that can bind to a nucleic acid fragment, and the nucleic acid fragment comprises a nucleotide sequence encoding the peptide of WSSV as claimed in claim 1;
   (ii) providing a tissue sample from an organism;

(iii) performing a hybridization reaction of a nucleic acid extracted from the tissue sample and the probe; and
(iv) detecting the nucleic acid fragment in the tissue sample to determine whether the organism was infected by the WSSV.

13. A method for detecting the WSSV, which comprises the following steps:
(I) providing a RT-PCR detection system, which comprises a mixed reagent containing primers for reverse transcription, primer pairs that can amplify a nucleic acid fragment, and the nucleic acid fragment comprises a nucleotide sequence encoding the peptide of WSSV as claimed in claim 1;
(II) providing a tissue sample from an organism, extracting its RNA and reverse transcribing the RNA into cDNA; and
(III) performing a PCR reaction using the cDNA of the tissue sample and the mixed reagent to amplify the nucleic acid fragment extracted from the tissue sample; and
(IV) detecting the nucleic acid fragment in the organism to determine whether the organism was infected by the WSSV.

\* \* \* \* \*

SEQUENCE LISTING

<160> NUMBER OF SEQ ID NOS: 2

<210> SEQ ID NO 1
<211> LENGTH: 82
<212> TYPE: PRT
<213> ORGANISM: white spot syndrome virus

<400> SEQUENCE: 1

Met Ala Thr Phe Gln Thr Asp Ala Asp Phe Leu Leu Val Gly Asp Asp
1               5                   10                  15

Thr Ser Arg Tyr Glu Glu Val Met Lys Thr Phe Asp Thr Tyr Glu Ala
            20                  25                  30

Val Arg Lys Ser Asp Leu Asp Asp Arg Val Tyr Met Val Cys Leu Lys
        35                  40                  45

Gln Gly Ser Thr Phe Tyr Leu Asn Gly Gly Ile Glu Glu Leu Arg Leu
    50                  55                  60

Leu Thr Gly Asp Ser Thr Leu Glu Ile Gln Pro Met Ile Val Pro Thr
65                  70                  75                  80

Thr Glu

<210> SEQ ID NO 2
<211> LENGTH: 249
<212> TYPE: DNA
<213> ORGANISM: white spot syndrome virus

<400> SEQUENCE: 2
atggccacct tccagactga cgccgatttc ttgctggtgg gggatgatac tagtagatat    60
gaagaagtga tgaagacttt tgatactgtt gaggcagtca ggaagagtga tctagatgac   120
cgtgtttaca tggtgtgcct aaagcaggga tctacttttg tcctcaatgg aggcatcgaa   180
gaattgcgtc ttttgactgg agattcaacg ctggagattc aacccatgat tgtgccaaca   240
acagaataa                                                           249